(12) United States Patent
Fujioka et al.

(10) Patent No.: US 6,793,649 B1
(45) Date of Patent: Sep. 21, 2004

(54) ABSORBENT ARTICLE FOR PREVENTION OF SIDEWARD LEAK

(75) Inventors: Yoshihisa Fujioka, Kagawa (JP); Ichiro Wada, Kagawa (JP); Satoshi Nozaki, Kagawa (JP); Takashi Maeno, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 0 days.

(21) Appl. No.: 09/274,197

(22) Filed: Mar. 22, 1999

(30) Foreign Application Priority Data

| Mar. 23, 1998 | (JP) | .......................................... 10-074057 |
| Mar. 23, 1998 | (JP) | .......................................... 10-074076 |
| Nov. 10, 1998 | (JP) | .......................................... 10-319136 |

(51) Int. Cl.$^7$ .......................... A61F 13/15; A61F 13/20
(52) U.S. Cl. ......................... 604/385.05; 604/385.101; 604/385.14; 604/387
(58) Field of Search ..................... 604/385.03, 385.05, 604/385.101, 385.14, 385.24, 386–396; 2/400–408; 602/67–73

(56) References Cited

U.S. PATENT DOCUMENTS

| 3,575,175 A | * | 4/1971 | McGuire ..................... 604/387 |
| 3,886,941 A | * | 6/1975 | Duane et al ................. 604/393 |
| 3,929,135 A | * | 12/1975 | Thompson |
| 4,324,246 A | * | 4/1982 | Mullane et al. |
| 4,405,310 A | | 9/1983 | Karami ....................... 604/383 |
| 4,938,756 A | | 7/1990 | Salek |
| 5,236,428 A | | 8/1993 | Zajaczkowski |
| 5,295,988 A | * | 3/1994 | Muckenfuhs et al. .. 604/385.05 |
| 5,460,624 A | * | 10/1995 | Ahr et al. ............. 604/385.05 |
| 5,556,393 A | * | 9/1996 | Ronnberg ................... 604/369 |
| H1724 H | * | 4/1998 | Ahr ..................... 604/385.101 |
| 5,910,137 A | * | 6/1999 | Clark et al. ................. 604/387 |

FOREIGN PATENT DOCUMENTS

| EP | 0319314 | 6/1989 |
| EP | 0 557 047 | 3/1997 |
| WO | 97/19663 | 6/1997 |

OTHER PUBLICATIONS

Search Report dated Dec. 20, 2000.

* cited by examiner

*Primary Examiner*—Karin M. Reichle
(74) *Attorney, Agent, or Firm*—Darby & Darby

(57) ABSTRACT

An absorbent article for wear inside of another absorbent article, which has a liquid-permeable facing layer that faces the wearer, and a backing layer that faces another absorbent article. The backing layer is formed from a liquid-impermeable sheet and as at least one opening. Alternatively, the backing layer is formed from a liquid-permeable sheet, and an absorbent core is interposed between the liquid-permeable facing layer and the backing layer.

4 Claims, 8 Drawing Sheets

ABSORBENT ARTICLE FOR PREVENTION OF SIDEWARD LEAK

FIELD OF THE INVENTION

The present invention relates to an absorbent article, including urine-absorbent pads, which is used inside a disposable diaper, and a sanitary napkin which is laid on top of the article to provide an absorbent article which exhibits excellent liquid-absorbing properties.

BACKGROUND OF THE INVENTION

A common means for caring for individuals suffering from incontinence is the use of an absorbent article, such as a urine-absorbent pad, worn inside a disposable diaper. A conventional urine-absorbent pad contains a facing layer and a backing layer, with an absorbent core interposed between the layers. The facing layer, which faces the wearer during use, is liquid-permeable. The backing layer, which faces the disposable diaper during use, is liquid-impermeable. The absorbent core is formed from crushed pulp or a mixture of crushed pulp and super absorbent polymer (SAP). In addition, the urine-absorbent pad has an adhesive layer which sticks to the inside of the disposable diaper for preventing the urine-absorbent pad from slipping out of place in the disposable diaper.

The urine-absorbent pad receives a liquid insult directly in the case of an incontinence episode, and has the capacity to retain an amount of urine excreted by an adult during one or two incontinence episodes. The pad must be replaced as it is saturated with urine, which depends on the frequency of episodes, in order to prevent liquid from moving to the disposable diaper. Thus, it is possible to avoid the replacement of the disposable diaper by frequently changing the wet pad. However, this is not always possible, such as during periods of sleep, when the urine-absorbent pad is left in place for a long time. After repeated liquid insults, the urine-absorbent pad cannot absorb additional liquid, which results in excess liquid leaking from the pad.

The problem is that the excess liquid flows to the side or periphery (which is in contact with the groin) rather than to the center of the disposable diaper (absorbent area of the disposable diaper), because the backing layer of the urine-absorbent pad is impermeable to liquid and faces the center of the disposable diaper. The periphery of the conventional disposable diaper does not absorb urine sufficiently, thereby causing it to leak at the sides of the diaper, which results in wet clothes or sheets. This same problem also occurs if two sanitary napkins are worn together on top of each other.

SUMMARY OF THE INVENTION

The present invention provides an absorbent article that prevents liquid from leaking from the sides of the article.

In one embodiment of the invention, a first absorbent article is worn inside of a second absorbent article, wherein the first article contains a liquid-permeable facing layer which is in contact with the wearer, and a backing layer which is in contact with a second absorbent article. Here, the backing layer is formed from a liquid-impermeable sheet and has at least one opening made therein. In addition, an absorbent core is interposed between the facing layer and the backing layer.

In another embodiment of the invention, a first absorbent article is worn inside of a second absorbent article, wherein the first article contains a liquid-permeable facing layer which is in contact with the wearer, and a liquid-permeable backing layer which is in contact with the second article, and an absorbent core interposed between the facing layer and the backing layer.

The absorbent article of the present invention is designed for wear inside of another absorbent article such as a disposable diaper, urine-absorbent pad, or sanitary napkin. The absorbent article absorbs a certain amount of liquid by the absorbent core but permits excess liquid which remains unabsorbed by the core to pass through the backing layer for absorption by another absorbent article such as a disposable diaper. Accordingly, the leakage of excess liquid from the side of the absorbent article is prevented.

The absorbent article can be modified such that the backing layer is provided with a liquid-impermeable covering sheet that can be removed at any time when necessary. With the covering sheet on, it stops the flow of urine; with the covering sheet removed, it permits the passage of urine. When frequent changes of the absorbent article are possible, such as during the daytime, it may be used with the covering sheet attached to prevent frequent replacement of the second absorbent article (e.g., a disposable diaper) used in combination with absorbent article. When frequent changes are unlikely, such as during periods of sleep, the absorbent article may be used with the covering sheet removed, thereby absorbing liquid efficiently and securely in combination with another absorbent article.

The absorbent article can be modified such that the backing layer is provided with an adhesive means for fastening the backing layer to another absorbent article. In such a structure, the absorbent article will not slip out of place, and the movement of liquid to the other absorbent article is ensured.

DETAILED DESCRIPTION OF THE INVENTION

Figure 1A:
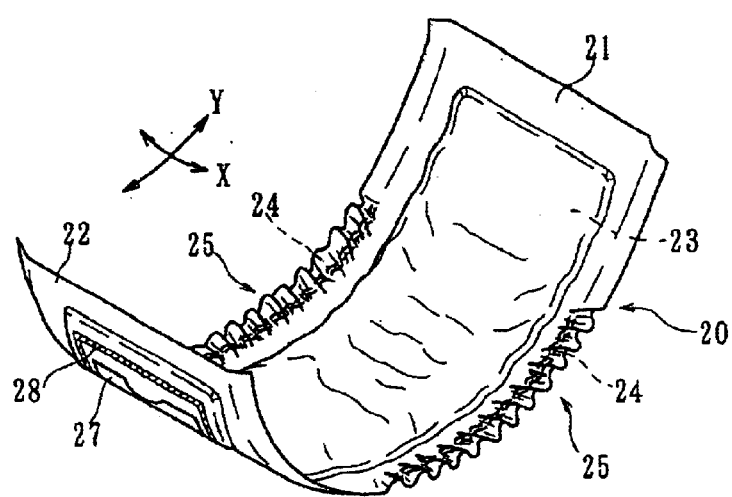
FIG. 1(A) is a perspective view showing a urine-absorbent pad as an example of an absorbent article according to the invention.
Figure 1B:
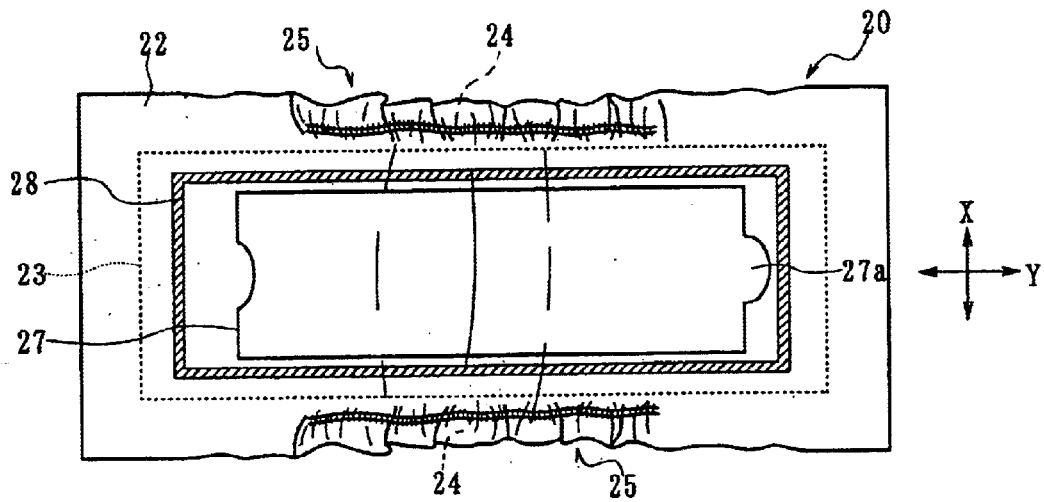
FIG. 1(B) is a plan view of the urine-absorbent pad shown in FIG. 1(A), as viewed from a backing layer, with a covering sheet attached.
Figure 1C:
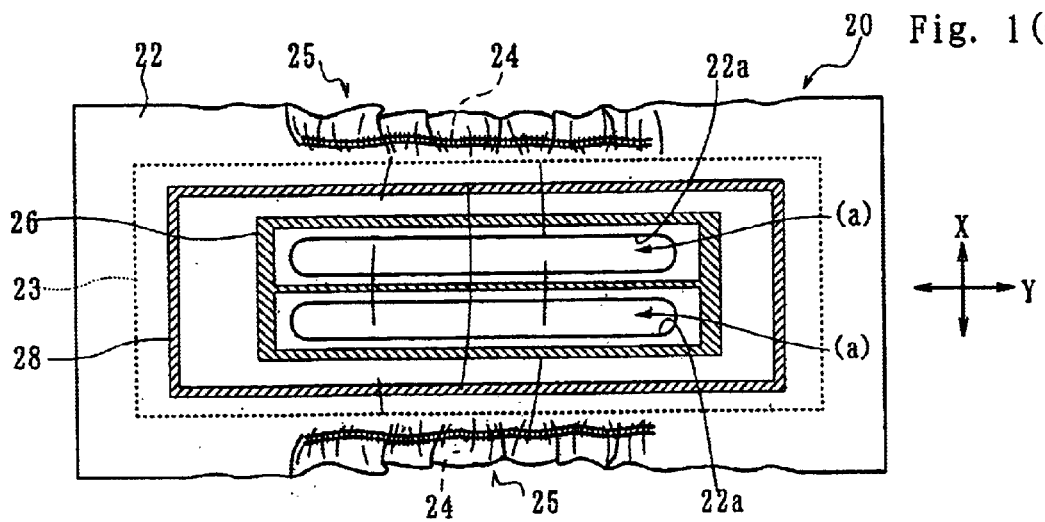
FIG. 1(C) is a plan view of the urine-absorbent pad shown in FIG. 1(B), as viewed from the backing layer, with the covering sheet removed.

A urine-absorbent pad, as an example of one embodiment of the absorbent article according to the invention, is shown in FIG. 1(A) (perspective view), FIG. 1(B) (plan view as viewed from a backing layer, with a covering sheet attached), and FIG. 1(C) (plan view as viewed from the backing layer, with the covering sheet removed).

The urine-absorbent pad 20 comprises a liquid-permeable facing layer 21 which faces the wearer during use, and a backing layer 22, which faces a disposable diaper during use, and an absorbent core 23 which is interposed between the two layers.

The facing layer 21 can be made from a nonwoven fabric of hydrophilic fibers hydrophobic fibers containing a hydrophilic surfactant, or the like. The facing layer 21 can be formed by various processes such as point bonding, through-air bonding, spun bonding, or spun lacing.

The backing layer 22 is made of a liquid-impermeable, breathable sheet of resin, such as polyolefin.

The absorbent core 23 is formed from crushed pulp or a mixture of crushed pulp and Super-Absorbent Polymer (SAP), and is covered with an absorbing sheet 23a such as tissue. (See FIG. 4.) The SAP can be made of polyacrylic acid, sodium polyacrylate, polyacrylamide, polyacrylonitrile, polyvinyl alcohol, an addition polymer of maleic anhydride, a polyether, a condensed polymer, a polysaccharide such as starch or cellulose, a protein such as collagen and the like. Examples of the SAPs include a cross-linked compound of sodium polyacrylate, a graft copolymer of starch having sodium polyacrylate and a graft copolymer of cellulose having polyacrylonitrile chains.

The absorbent core 23 is rectangular in shape as indicated by the dotted lines in FIGS. 1(B) and 1(C). It may also take on an hourglass shape. With the absorbent core 23 interposed between the facing layer 21 and the backing layer 22, the layers are then bonded together with a hot-melt adhesive, or the like, along the periphery of the absorbent core 23.

As used herein, the "absorbing area" refers to the area which is surrounded by the dotted lines in FIGS. 1(B) and 1(C) and the area of the absorbent core 23.

The urine-absorbent pad 20 has elastic members 24 which are disposed between the facing layer 21 and the backing layer 22 and extend in the lengthwise direction (Y direction) of the urine-absorbent pad 20. The elastic members 24 exist in side areas where the absorbent core 23 is absent (i.e., outside of the absorbing area in the widthwise direction (X direction) of the urine-absorbent pad 20). The elastic members 24 are bonded to the facing layer 21 and the backing layer 22 when stretched in the Y direction (with a certain elongation percentage). In their free state, they shrink in the Y direction, causing the facing layer 21 and the backing layer 22 to form gathers 25 on both side areas of the urine-absorbent pad 20 in the X direction.

As shown in FIG. 1(C), the backing layer 22 is made of a liquid-impermeable resin sheet and has openings 22a, through which openings the absorbing sheet 23a (e.g., tissue) covering the absorbent core 23 is exposed. In this embodiment, the openings 22a constitute liquid-passing areas indicated by (a).

The openings 22a (or the liquid-passing areas (a)) are arranged side by side approximately at the center of the absorbing area in the widthwise direction (X direction) and are elongated parallel to each other in the lengthwise direction (Y direction). In other words, they are situated substantially at the center of the absorbing area. The area of the openings 22a is smaller than that of the absorbing area.

The backing layer 22 has an adhesive layer 26 as an adhesive means. The adhesive layer 26 is formed on the backing layer 22 in such a way as to surround the openings 22a individually. This adhesive layer 26 aids in fastening a covering sheet 27 to the outside of the backing layer 22, as shown in FIG. 1(B). Thus the covering sheet 27 closes the openings 22a. In other words, the adhesive layer 26 surrounds the openings 22a completely, and the covering sheet 27 is bonded to this adhesive layer 26. Therefore, with the covering sheet 27 attached, the liquid-passing areas (a) are closed and the backing layer 22 of the urine-absorbent pad 20 prevents liquid from passing through.

The covering sheet 27 is made of a liquid-impermeable and breathable sheet of resin such as polyolefin, like the backing layer 22. The adhesive layer 26 is formed from a gum adhesive or acrylic resin to permit removal of the covering sheet 27 at any time from the backing layer 22, and retains a certain adhesive power even after the covering sheet 27 has been removed. When the urine-absorbent pad 20 is used in combination with a disposable diaper, the adhesive layer 26 (with the covering sheet 27 removed) adheres to the inside of the disposable diaper. As a result, the urine-absorbent pad 20 is prevented from slipping out of place. In addition, because the urine-absorbent pad 20 is in contact with the disposable diaper, the passage of urine to the disposable diaper is secured.

The covering sheet 27 has a tab 27a formed at its end. This tab 27a is not bonded to the backing layer 22.

The urine-absorbent pad 20 is used in combination with a disposable diaper 1 (shown in FIGS. 2 and 3) one over the other, with the former placed inside of the latter. The disposable diaper 1 has the shape of an hourglass and consists of a front part 1A (faces the abdomen of the wearer in use), a rear part 1B (faces the hip or back of the wearer in use), and a middle part 1C (faces the groin in use).

The disposable diaper 1 has a liquid-permeable inner layer 2 and a liquid-impermeable outer layer 3, with an absorbent body 4 interposed between them. The absorbent body 4, which has the shape of an hourglass, is formed from crushed pulp or a mixture of crushed pulp and SAP and is enclosed with an absorbing sheet such as tissue.

The middle part 1C of the disposable diaper 1 has longitudinally extending elastic bodies 5 at its side edges and between the inner layer 2 and the outer layer 3, so that the elastic bodies 5 form gathers 6 when they shrink.

The inner layer 2 of the rear part 1B has fasteners (hooks) 7 at its edges. The outer layer 3 of the front part 1A also has fasteners (piles) 8. To wear the disposable diaper 1, the fasteners 7 and 8 are engaged with each other around the waist of the wearer.

Although the disposable diaper 1 described herein is an example of the open type, the urine-absorbent pad 20 of the invention may also be used in combination with a disposable diaper of the pants type in which the front part 1A and the rear part 1B are bonded together at their edges.

If the user can frequently change the absorbent pad, for example, during the daytime, the urine-absorbent pad 20 is used with the covering sheet 27 attached. In this embodiment, as shown in FIG. 1(B), the openings 22a in the backing layer 22 remain closed by the covering sheet 27 which is fixed by the adhesive layer 26 formed around the openings 22a. Therefore, the openings 22a (liquid-passing areas (a)) are completely closed and urine does not leak from the urine-absorbent pad 20 through the openings 22a.

Figure 2:
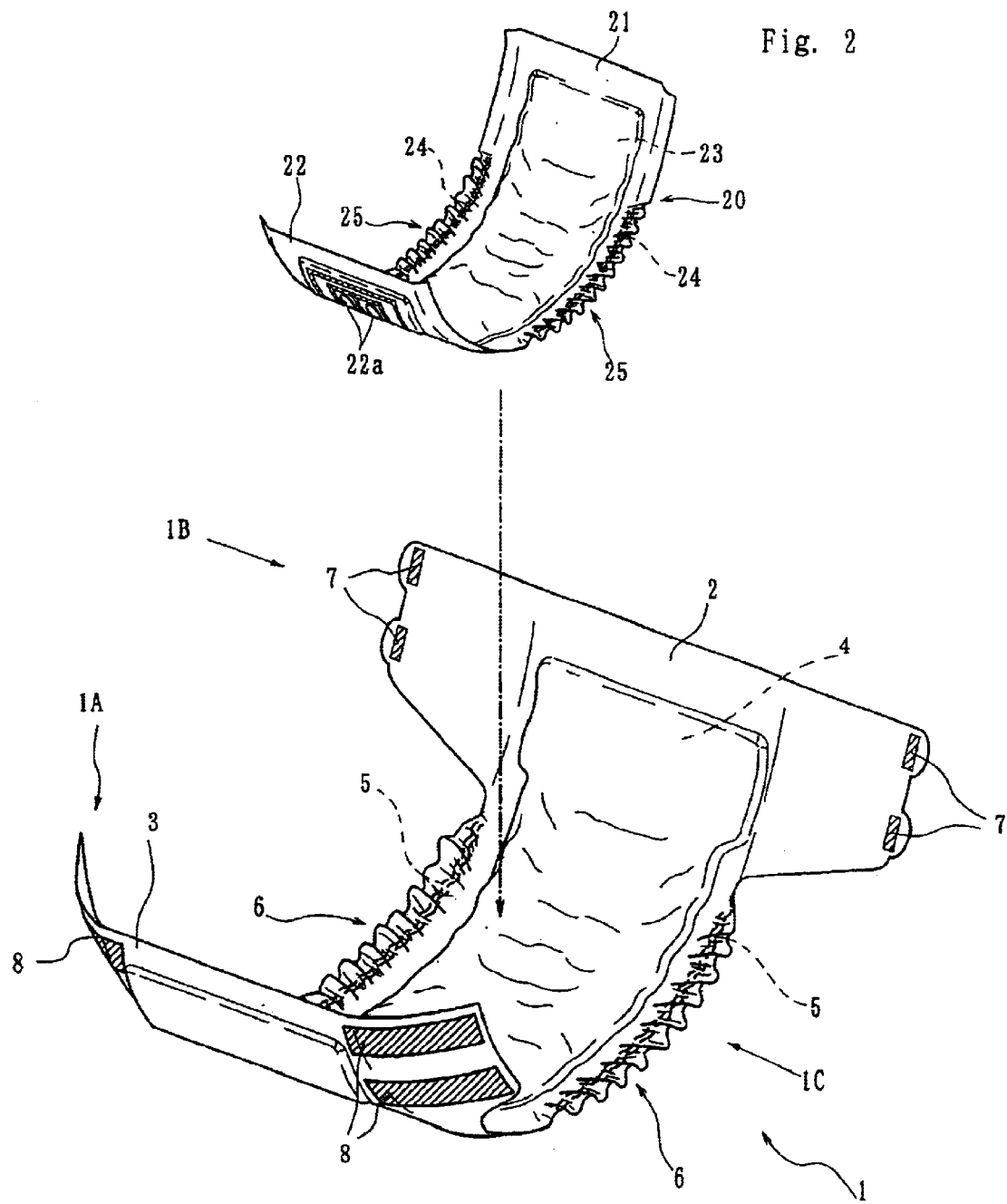
FIG. 2 is a perspective view which illustrates how the urine-absorbent pad of FIG. 1(A) is used in combination with a disposable diaper.
Figure 3:
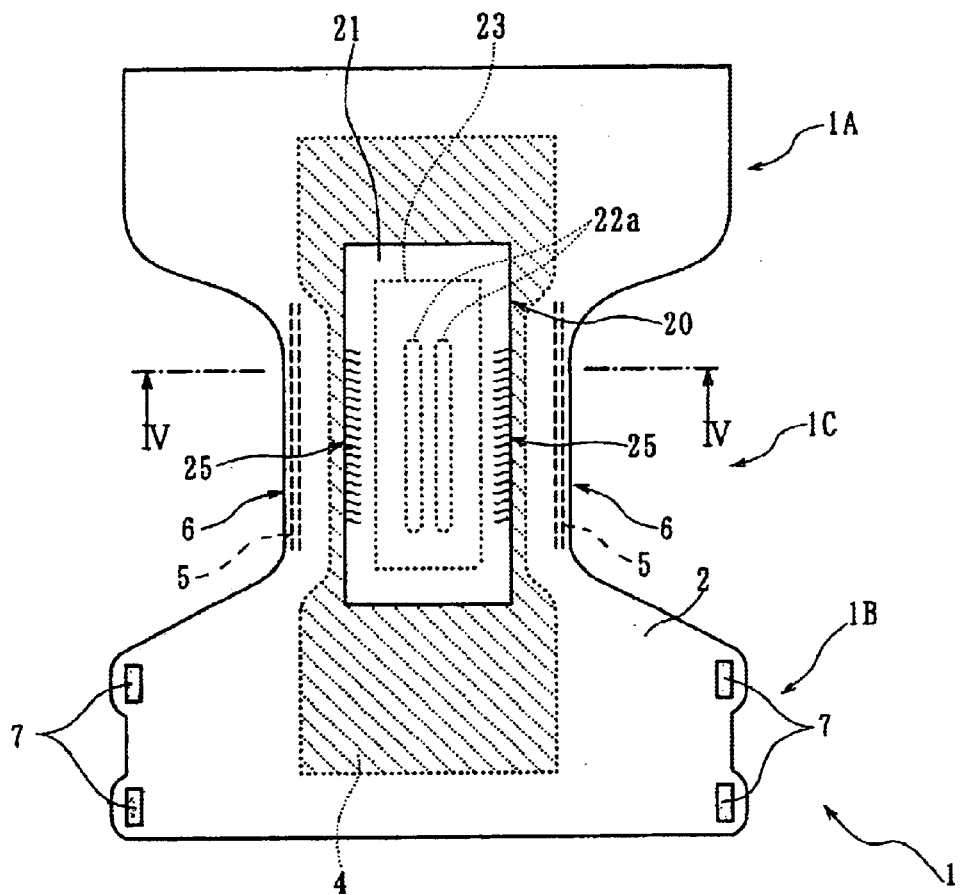
FIG. 3 is a plan view which illustrates how the urine-absorbent pad shown in FIG. 1(A) is used in combination with a disposable diaper.

The urine-absorbent pad 20 is placed on the inner layer 2 of the disposable diaper 1, with the backing layer 22 facing the disposable diaper 1, as shown in FIGS. 2 and 3. In this embodiment, to prevent the urine-absorbent pad 20 from slipping out of place, the backing layer 22 may be provided with another adhesive layer 28 as another adhesive means which does not face the covering sheet 27, as shown in FIG. 1(B), and adheres to the inner layer 2 of the disposable diaper 1. Alternatively, the adhesive layer 28 may be formed on the covering sheet 27. In this case, the adhesive force by the adhesive layer 28 between the covering sheet 27 and the inner layer 2 should be weaker than the force by the adhesive layer 26 between the backing layer 22 and the covering sheet 27, so that the covering sheet 27 will not accidentally be removed from the urine-absorbent pad 20 when the urine-absorbent pad 20 is removed from the disposable diaper 1.

The urine-absorbent pad 20, with the covering sheet 27 attached, functions in the same way as a conventional urine-absorbent pad. If the absorbent core 23 has a capacity to absorb about 300 cc of urine, there will be little leakage from the urine-absorbent pad 20 after urinary incontinence (one or two episodes), assuming that about 150 cc of urine is excreted each time. If the urine-absorbent pad 20 is replaced whenever incontinence occurs, little or no urine reaches the absorbent body 4 of the disposable diaper 1. Thus, the disposable diaper 1 can be used continuously without being soiled.

Alternatively, when the ability to change the urine absorbent pad is limited, for example, during periods of sleep, the urine-absorbent pad 20 is placed on the disposable diaper 1 (as shown in FIGS. 2 and 3), with the covering sheet 27 removed (as shown in FIG. 1(C)). The covering sheet 27 can be removed easily by pulling the tab 27a projecting from it as shown in FIG. 1(B). After the covering sheet 27 has been removed, the adhesive layer 26 on the backing layer 22 is exposed and adheres to the inner layer 2 of the disposable diaper 1, thereby preventing the urine-absorbent pad 20 from slipping out of place. Incidentally, if the adhesive layer 28 is formed on the backing layer 22, it also helps the urine-absorbent pad 20 to adhere to the disposable diaper 1.

When the covering sheet 27 is removed, the openings 22a in the backing layer 22 open to form the liquid-passing areas (a), and the absorbent core 23 is exposed through these openings 22a. Therefore, when the urine-absorbent pad 20 is placed on the disposable diaper 1 as shown in FIG. 3, the absorbent core 23 faces the inner layer 2 of the disposable diaper 1 through the openings 22a.

The flow of urine in the embodiment described above is illustrated in FIG. 4, which is a sectional view taken along the line IV—IV in FIG. 3. The absorbent core 23 of the urine-absorbent pad 20 absorbs a large portion of urine but permits any remaining urine to pass through the openings 22a (liquid-passing areas (a)) in the backing layer 22 to be absorbed by the absorbent body 4 of the disposable diaper 1. Assuming that the amount of urine is about 150 cc when incontinence occurs once, about 100 cc will be absorbed by the absorbent core 23 of the urine-absorbent pad 20 and the remaining 50 cc will be absorbed by the absorbent body 4 of the disposable diaper 1. Upon passing through the openings 22a, the urine moves mostly to the center of the absorbent body 4 where it is absorbed. Therefore, urine will not leak at the sides or the gathers 6 of the disposable diaper 1.

In the case where incontinence occurs several times (e.g., more than two times) and the total amount of urine is greater than 300 cc, e.g., about 450 cc, the absorbent core 23 of the urine-absorbent pad 20 absorbs about 300 cc of urine and the absorbent body 4 of the disposable diaper 1 absorbs the remaining 150 cc of urine. Even if incontinence is more frequent, excess urine will move to the absorbent body 4 of the disposable diaper 1. Therefore, side leakage of urine can be effectively prevented even in the case of frequent incontinence.

The absorbent core 23 of the urine-absorbent pad 20 becomes almost saturated with urine after incontinence has occurred two or three times. If the urine-absorbent pad 20 is replaced at this stage, the disposable diaper 1 is still usable because the absorbent body 4 of the disposable diaper 1 has not yet absorbed urine to its full capacity. Therefore, frequent replacement of the disposable diaper 1 can be prevented.

Figure 4:
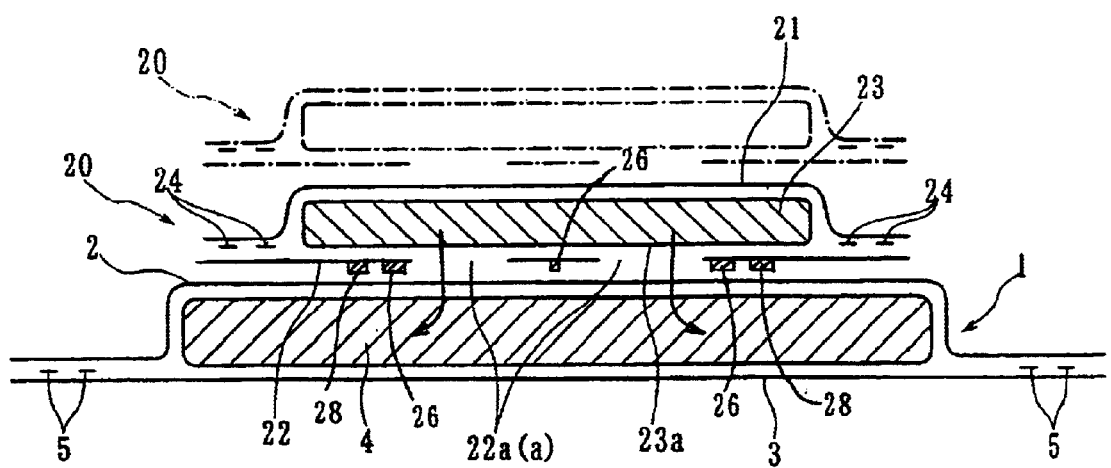
FIG. 4 is a schematic sectional view taken along the line IV—IV in FIG. 3.

Two or more urine-absorbent pads 20 (with the covering sheet 27 removed) may be placed on the inner layer 2 of the disposable diaper 1, as indicated by dotted lines in FIG. 4. In this embodiment, urine is absorbed by each absorbent core 23 of the urine-absorbent pad 20. Thus, it is possible to increase the capacity for absorbing urine and to prevent soiling of the disposable diaper 1 by the urine even where there is frequent incontinence.

Figure 5:
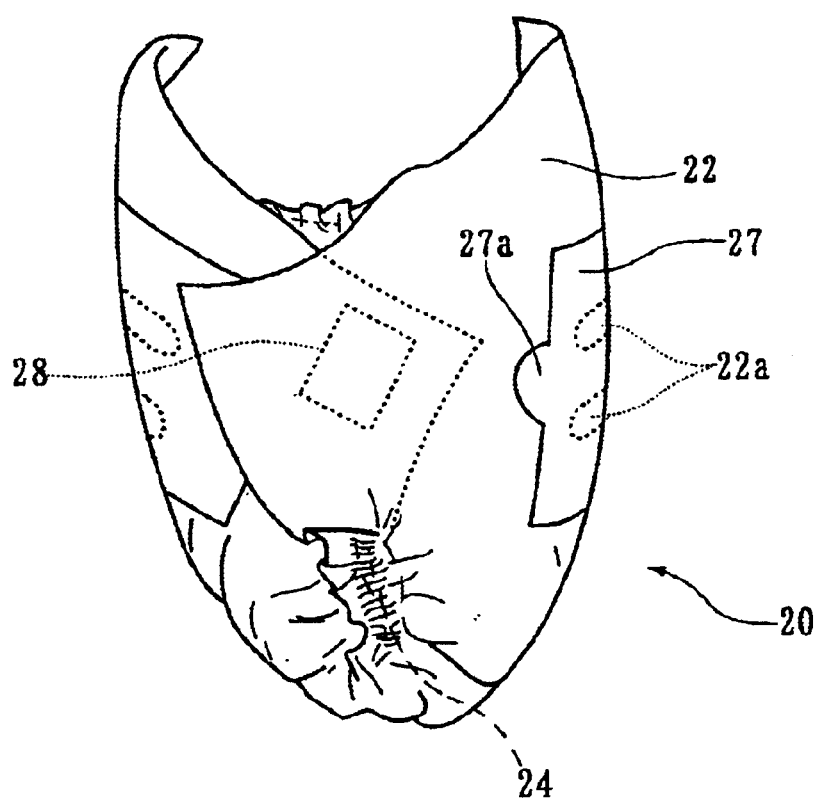
FIG. 5 is a perspective view of the urine-absorbent pad shown in FIG. 1(A) which is folded for use by a man, with its shape modified so as to enclose a penis.

The urine-absorbent pad 20 described above is designed to be used in a stretched form, having a slight curve. However, it may be so folded as to enclose a penis as shown in FIG. 5. In this embodiment, the urine-absorbent pad 20 is folded into a cone shape with the facing layer 21 inside and the lengthwise edges overlapped. This embodiment may be accomplished by bonding the outside of one lengthwise edge of the urine-absorbent pad 20 to the inside of the other lengthwise edge of the urine-absorbent pad 20 using an adhesive layer 28 (such as double-sided adhesive tape). The penis is inserted into the conically folded pad, which pad is subsequently covered with the disposable diaper 1.

If the pad can be changed frequently, the urine-absorbent pad 20, which has been folded for males, is used with the openings 22a closed by the covering sheet 27.

When frequent changing of the pad is not available, the urine-absorbent pad 20 thus folded for males is used with the covering sheet 27 removed so that the openings 22a of the backing layer 22 are exposed. In this case, the urine-absorbent pad 20 should be positioned such that the openings 22a, face the inner layer 2 of the disposable diaper 1. The result is the same as that explained above with reference to FIG. 4. The excess urine which is not absorbed by the absorbent core 23 of the urine-absorbent pad 20 passes through the openings 22a to be absorbed by the absorbent body 4 of the disposable diaper 1. Thus, it is possible to cope with frequent episodes of incontinence.

Figure 6A:
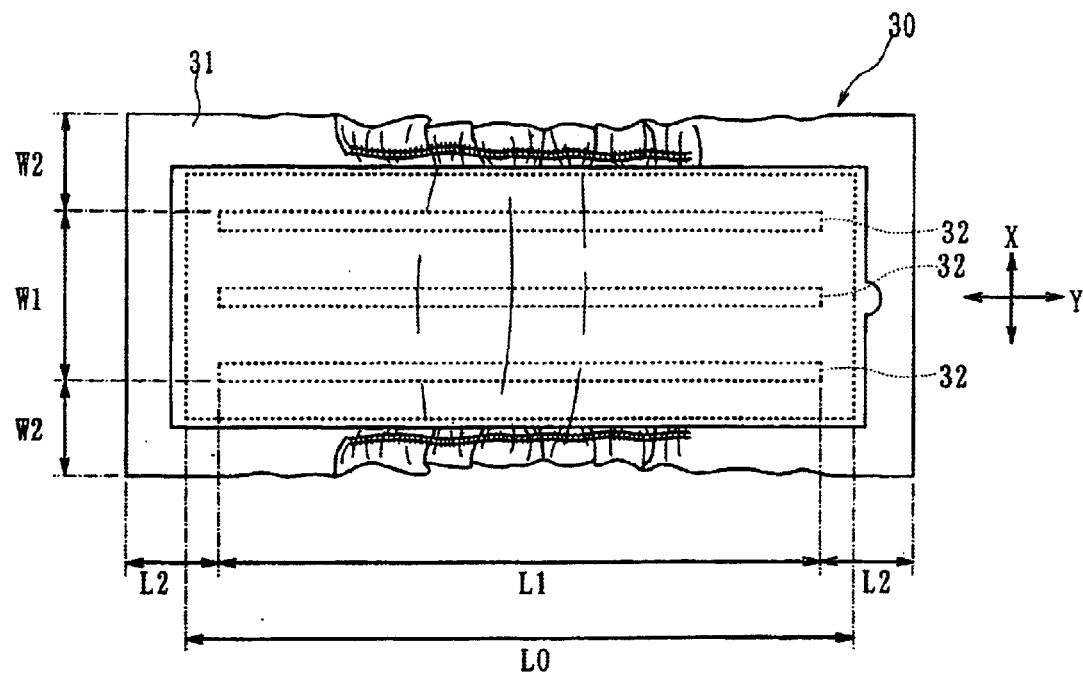
FIG. 6(A) is a plan view of a urine-absorbent pad as another example of the absorbent article according to the invention, as viewed from a backing layer, with a covering sheet attached.
Figure 6B:
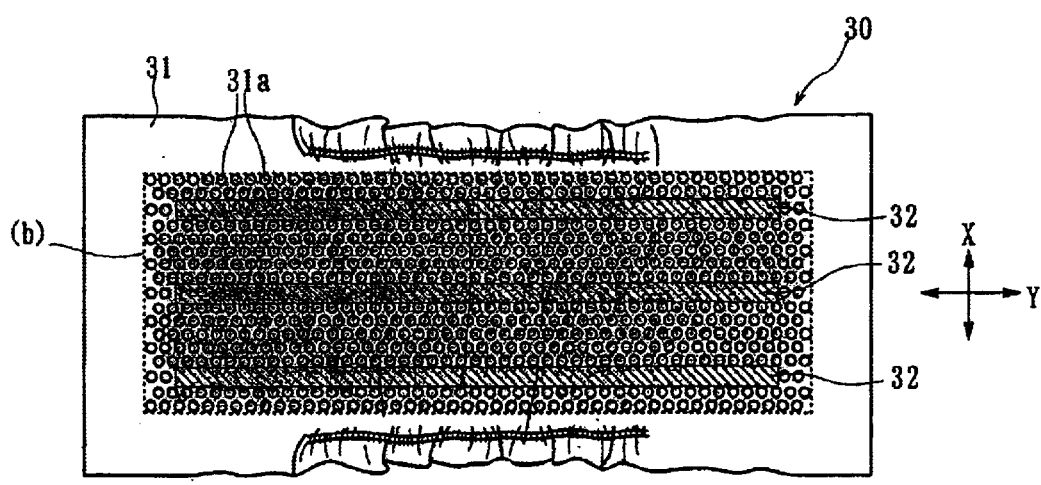
FIG. 6(B) is a plan view of the urine-absorbent pad shown in FIG. 6(A), as viewed from the backing layer, with the covering sheet removed.

In another embodiment of the absorbent article of the invention, the urine-absorbent pad may be modified as shown in FIGS. 6(A) and 6(B). FIG. 6(A) is a plan view of the urine-absorbent pad, as viewed from the backing layer. FIG. 6(B) is a plan view of the urine-absorbent pad, with the covering sheet removed.

A urine-absorbent pad 30 shown in FIG. 6(A) is similar in structure to the urine-absorbent pad 20 shown in FIG. 1(A).

It has a facing layer and a backing layer, with an absorbent core interposed between them, and has gathers (formed by elastic members extending in the Y direction) on both of the side areas thereof. Therefore, it is made of the same materials and is used in the same manner as the absorbent pads described above.

The urine-absorbent pad 30 has a backing layer 31 which is made of liquid-impermeable resin film (such as polyolefin), similar to the backing layer 22 of the urine-absorbent pad 20. The backing layer 31 has a number of openings 31a which almost entirely cover the absorbent core (or absorbing area) as shown in FIG. 6(B). In other words, this embodiment is constructed such that the liquid passing area (b) substantially coincides with the absorbing area (the area containing the absorbent core). Incidentally, the openings 31a may be formed in the entire area of the backing layer 31 although they are confined to the absorbing area in this particular embodiment.

Each of the openings 31a are preferably circular, with a diameter larger than 0.5 mm, preferably larger than 1 mm. The openings 31a are preferably arranged with a pitch greater than 1 mm, preferably greater than 1.5 mm. The advantage of establishing the size and pitch of the openings 31a as described above is that the liquid-passing area (b) of the urine-absorbent pad 30 can be recognized visibly. This avoids the possibility of mistaking an ordinary urine-absorbent pad, in which the backing layer does not have the liquid-passing area, for one of the invention.

In the case of the urine-absorbent pad 30 in which the openings 31a are formed so as to almost entirely cover the absorbent core (or the absorbing area), it is necessary to provide an adhesive layer 32 as described below to ensure proper adhesion between the backing layer 31 of the urine-absorbent pad 30 and the inner layer 2 of the disposable diaper 1. Thus, the adhesive layer 32 is preferably formed in the absorbing area (or the area in which the absorbent core exits). Assuming that the area in which the adhesive layer 32 is formed has dimensions of L1 by W1, the length L1 (Y direction) should be equal to or smaller than the length L0 of the absorbent core but greater than 50% of the length L0. In addition, it is preferred that the total area of the adhesive layer 32 is less than 60% of the area of the absorbent core in order to ensure the smooth flow of urine from the backing layer 31 to the disposable diaper 1.

When the urine-absorbent pad 30 is used in combination with a disposable diaper 1 for adults, it is preferred that the area (L1 by W1) of the adhesive layer 32 includes the center of the urine-absorbent pad 30 (in the widthwise direction) and the width W1 is within the range of 40 to 50 mm. The adhesive layer 32, formed as described above, prevents the urine-absorbent pad 30 and the disposable diaper 1 from displacing each other when they shrink in the widthwise direction (X direction) in the wearer's groin. In addition, the adhesive layer 32 has little tendency to stick to the wearer's skin and hair.

It is preferable for the area (L1 by W1) in which the adhesive layer 32 is formed to have a distance W2 of at least 30 mm from the edges of the adhesive layer 32 to the edge of urine-absorbent pad 30, and a length L2 of at least 30 mm from the edge of the adhesive layer 32 to the edge of the urine-absorbent pad 30. The adhesive layer 32 formed in this manner has little tendency to stick to the wearer's skin and hair when the edges of the urine-absorbent pad 30 are turned up to the groin.

Incidentally, in the embodiment of the urine-absorbent pad 20 shown in FIG. 1(C), it is preferable for the adhesive layer 26 to be formed in the same region as for the adhesive layer 32.

Figure 7A:
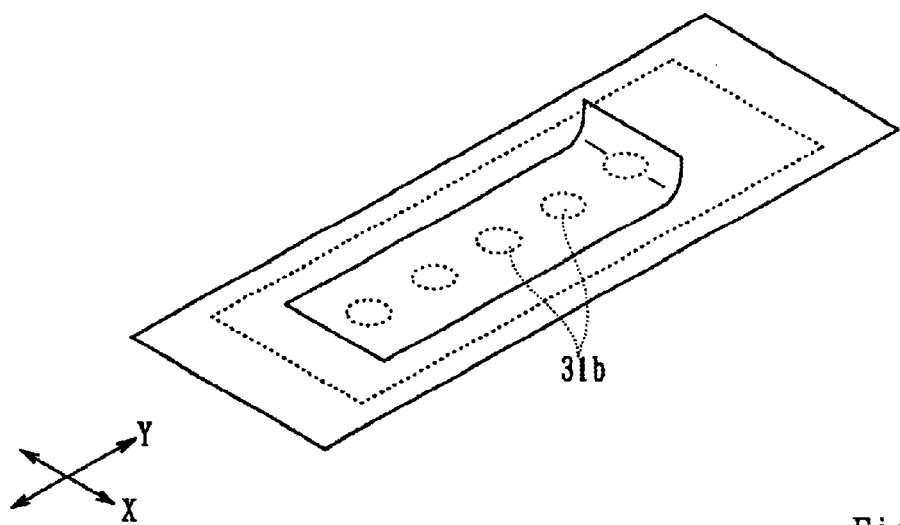
FIGS. 7(A) and 7(B) are perspective views of examples of openings.
Figure 7B:
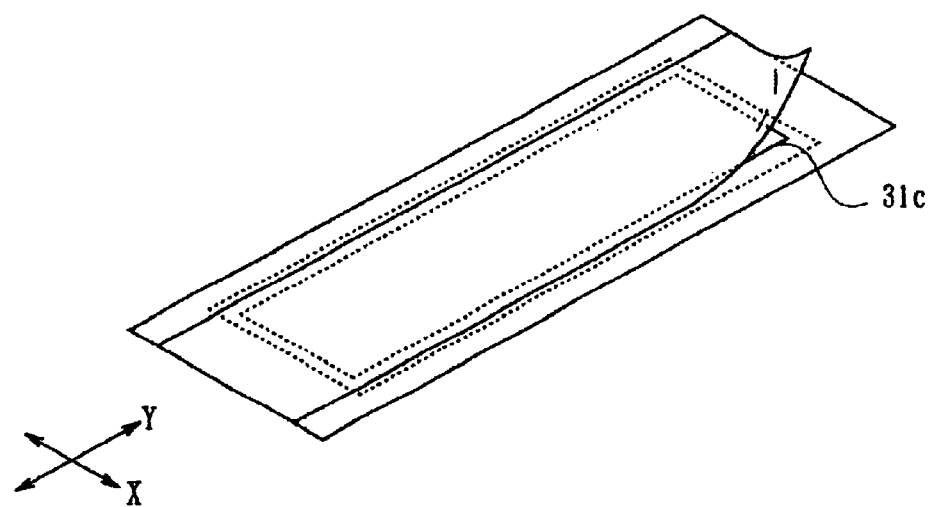

The openings may be positioned and shaped as shown in FIGS. 7(A) and 7(B). In FIG. 7(A), comparatively large round (or elliptic) holes 31b are formed in a line extending in the lengthwise direction (Y direction) and approximately at the center of the urine-absorbent pad. In FIG. 7(B), one large hole 31c is formed almost equal to the absorbing area (or the area in which the absorbent core exists).

Figure 8A:
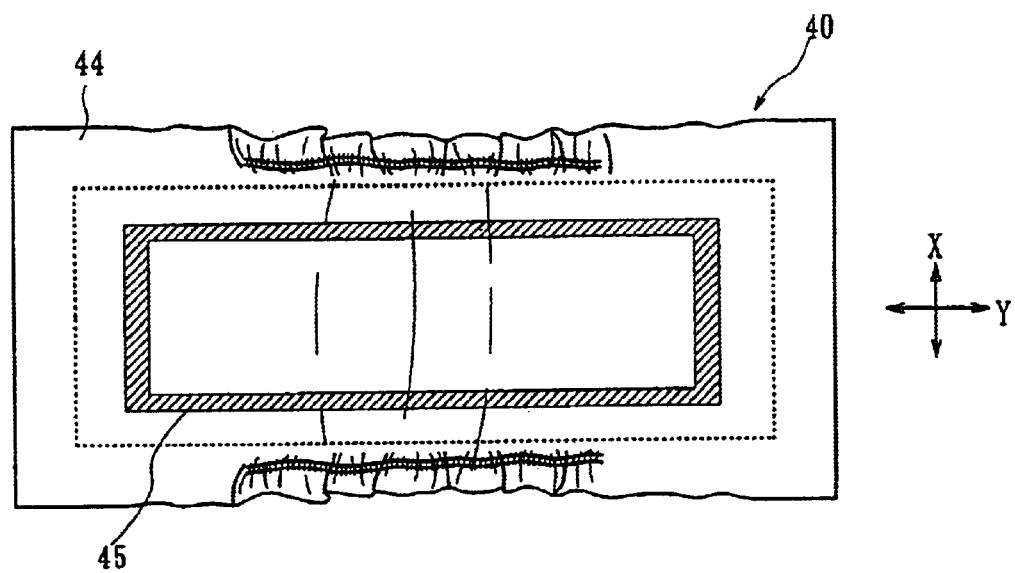
FIG. 8(A) is a plan view of a urine-absorbent pad as another example of the absorbent article according to the present invention, as viewed from a backing layer, with a covering sheet attached.
Figure 8B:
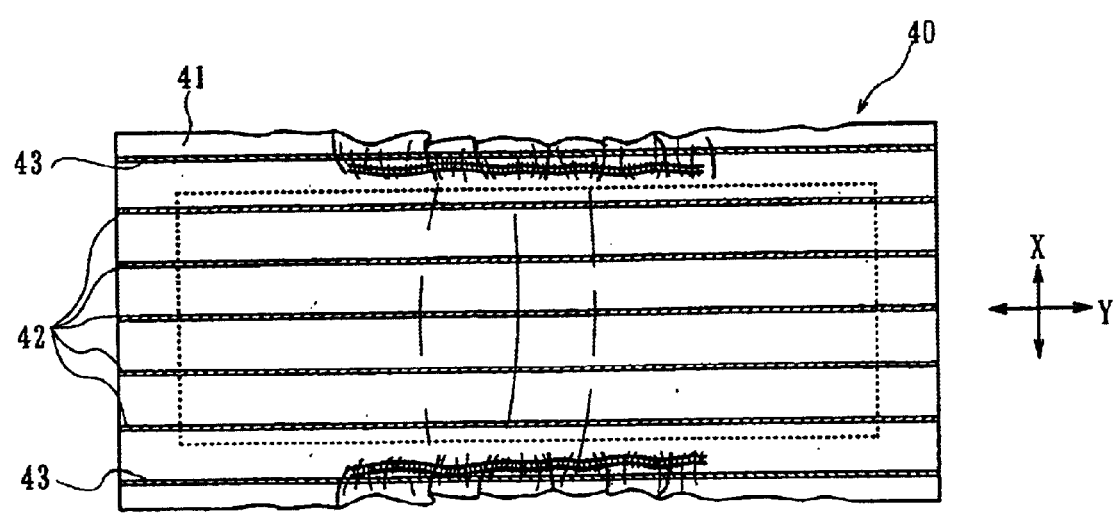
FIG. 8(B) is a plan view of the urine-absorbent pad shown in FIG. 8(A), as viewed from the backing layer, with the covering sheet removed.

FIGS. 8(A) and 8(B) show another embodiment of the absorbent article according to the present invention embodied in a urine-absorbent pad. FIG. 8(A) is a plan view of a urine-absorbent pad as viewed from the backing layer thereof, with the covering sheet attached. FIG. 8(B) is a plan view of the urine-absorbent pad as viewed from the backing layer thereof, with the covering sheet removed.

A urine-absorbent pad 40 shown in FIG. 8(A) is similar in structure to the urine-absorbent pad 20 shown in FIG. 1(A). Thus, it contains a liquid-permeable facing layer and a backing layer, with an absorbent core interposed between them, and has gathers (formed by elastic members extending in the Y direction) on both of the side areas thereof. It is used in the same manner as described above.

The urine-absorbent pad 40 has a backing layer 41 which is made of liquid-permeable fiber-interlaced nonwoven fabric of hydrophobic fibers and/or hydrophilic fibers with or without water-absorbing fibers such as rayon fibers. Therefore, the backing layer 41 as a whole is permeable to liquid and constitutes the liquid-passing area.

On the backing layer 41 strips are formed of a first adhesive layer 42 which extend parallel in the lengthwise direction (Y direction) at certain intervals in the widthwise direction (X direction), as shown in FIG. 8(B). The first adhesive layer 42 as a first adhesive means is formed at the center of the backing layer 41 in the widthwise direction, so that it is positioned within the absorbing area in the widthwise direction. Preferably, the total area of the first adhesive layer 42 is adequately established relative to the area of the backing layer 41 so that it will not adversely affect the liquid passing function of the backing layer 41.

Incidentally, the coating pattern of the first adhesive layer 42 is not limited to a striped pattern, but may take on any shape, such as dots or spirals.

In addition, the backing layer 41 has second adhesive layers 43, as a second adhesive means, which are formed at the side areas thereof (gathers are included in the side areas) and extend in the lengthwise direction (Y direction). The first adhesive layer 42 and the second adhesive layers 43 allow a single covering sheet 44 to be attached to and cover the entire surface of the liquid-permeable backing layer 41, as shown in FIG. 8(A). The covering sheet 44 is formed from a liquid-impermeable, breathable resin sheet such as polyolefin. Since the side portions of the covering sheet 44 in the widthwise direction are attached to the backing layer 41 by the second adhesive layers 43, the covering sheet 44, together with the backing layer 41 and the facing layer, form gathers by the shrinking force of the elastic members.

The first adhesive layer 42 preferably exhibits a prescribed adhesive force when the covering sheet 44 is removed. To accomplish this, the first adhesive layer 42 is formed by coating with a gum adhesive or acrylic resin. In contrast, the second adhesive layers 43 should have a moderate adhesive force, such that the covering sheet 44 can be removed easily by hand and should exhibit very little adhesive force once the covering sheet 44 has been removed. To accomplish this, the second adhesive layers 43 are formed from a hot-melt adhesive of EVA or polyolefin. Thus, the second adhesive layers 43 are stronger than the first adhesive layer 42 in adhering to the covering sheet 44, but exhibit a weaker adhesive force than the first adhesive layer 42 once the covering sheet 44 has been removed.

The first adhesive layer 42 and the second adhesive layers 43, as described above, prevent the covering sheet 44 from inadvertently being removed or peeled off, because the side portions of the covering sheet 44 are attached to the backing layer 41 by the second adhesive layers 43. When the covering sheet 44 is removed from the backing layer 41, the first adhesive layer 42 (in a striped pattern) appears at the center (in the widthwise direction) of the backing layer 41 and adheres to the inside of the disposable diaper 1, thereby preventing the urine-absorbent pad from slipping out of place. In this case, the second adhesive layers 43 exhibit very little adhesive force and therefore do not adhere to the wearer's skin or hair even when the side areas of the urine-absorbent pad 40 are facing the groin.

A third adhesive layer 45 as a third adhesive means may be formed on the covering sheet 44 as shown in FIG. 8(A). When the urine-absorbent pad 40 is used with the covering sheet 44 attached, and in combination with the disposable diaper 1, the inner layer 2 of the diaper 1 is fastened (bonded) to the third adhesive layer 45 so that the urine-absorbent pad 40 stays in position. It is important that the adhesive force of the third adhesive layer 45, when applied to the inner layer 2, is weaker than that of the second adhesive layers 43 applied to the covering sheet 44. This embodiment aids in preventing inadvertent removal of the covering sheet 44 from the backing layer 41 when the urine-absorbent pad 40 is removed from the disposable diaper 1.

Figure 9:
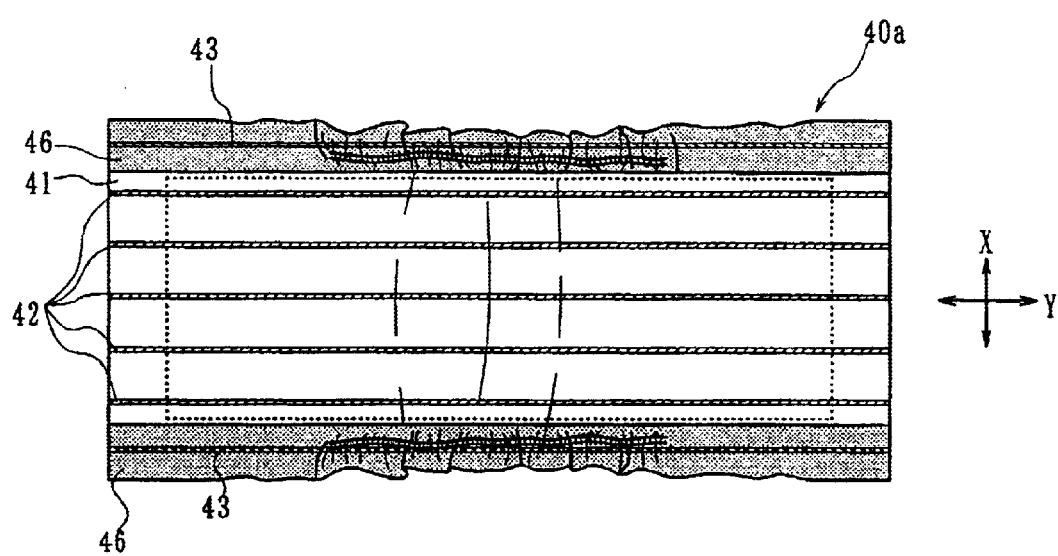
FIG. 9 is a plan view of another embodiment of the urine-absorbent pad shown in FIG. 8(A), with the covering sheet removed.

Another embodiment of the urine-absorbent pad 40a is shown in FIG. 9, which is a plan view showing the pad with the covering sheet removed. The urine-absorbent pad 40a is identical in structure to the urine-absorbent pad 40 described above, except that the backing layer 41 has side layers 46 which are formed from a liquid-impermeable resin sheet or from a hydrophobic, highly water-resistant nonwoven fabric and the second adhesive layers 43, formed on the side layers 46. That is, the side layers 46 are disposed on both side areas of the backing layer 41 in the widthwise direction and between the backing layer 41 and the covering sheet. The side layers 46 are bonded to the backing layer 41 by a hot-melt adhesive. With the covering sheet removed, the side layers 46 appear on both the side areas of the urine-absorbent pad 40a including the gathers.

When this embodiment of the urine-absorbent pad 40a is used with the covering sheet removed, and in combination with the disposable diaper 1, the liquid-impermeable side layers 46 prevent urine from flowing to the disposable diaper 1, at both side areas of the urine-absorbent pad 40a. Consequently, urine passing through the absorbent core of the urine-absorbent pad 40a reaches the center of the absorbent body 4 of the disposable diaper 1. Thus, urine has little or no tendency to leak from the sides of the disposable diaper 1.

While the invention has been described in detail in its preferred embodiments, it should be understood that other embodiments may be prepared within the scope of the claims.

For example, an adhesive layer is not the only means that can be used to fasten together the urine-absorbent pad and the inner layer of the disposable diaper. It may be replaced by a mechanical means such as hooks attached to the backing layer, which engage with the nonwoven fabric of the inner layer of the disposable diaper to prevent the urine-absorbent pad from slipping out of place.

In the embodiment of the urine-absorbent pad for males only, the pad may be pre-formed in the shape of a cone or cylinder during the production process, with the liquid-passing area formed on the outside thereof.

The absorbent article of the present invention is not limited to the urine-absorbent pad, but also includes other absorbent articles, including sanitary napkins and may be used in combination with one another.

As used herein, "comprises" and all its grammatical forms specifies the presence of stated features, integers, steps or components, but does not preclude the presence or addition of one or more other features, integers, steps, components or groups thereof.

What is claimed is:

1. An absorbent article for wear inside another absorbent article, comprising:

a liquid-permeable facing layer which faces a wearer during use;

a liquid-permeable backing layer which faces the other absorbent article during use;

an absorbent core interposed between the facing layer and the backing layer;

first and second adhesives disposed on the backing layer, the second adhesive being located on both sides of the absorbent article lying opposite one another in a widthwise direction thereof, the first adhesive being located closer to a center of the absorbent article in the widthwise direction thereof than the second adhesive; and a liquid-impermeable covering sheet removably attached to the backing layer through the first and second adhesive to thereby cover the entire surface of the backing layer opposite the surface adjacent to the core, an adhesive force of the second adhesive to the convering sheet being stronger than an adhesive force of the first adhesive to the covering sheet;

wherein when the covering sheet is removed to expose both the first and second adhesive during use, the first adhesive exhibits adhesive force to the other absorbent article than the second adhesive.

2. The absorbent article of claim 1, wherein the first adhesive is an adhesive in a striped pattern.

3. The absorbent article of claim 1, wherein the second adhesive is a hot-melt adhesive.

4. The absorbent article of claim 3, wherein the covering sheet comprises a third adhesive which exhibits an adhesive force to the other absorbent article when the absorbent article is applied to the other absorbent article, without removing the covering sheet, wherein the adhesive force of the third adhesive to the other absorbent article is weaker than the adhesive force of the second adhesive to the covering sheet.

\* \* \* \* \*